(12) United States Patent
Corbitt, Jr. et al.

(10) Patent No.: US 7,891,359 B2
(45) Date of Patent: *Feb. 22, 2011

(54) SURGICAL DRAPE

(76) Inventors: John D. Corbitt, Jr., 142 JFK Dr., Atlantis, FL (US) 33462; Albert N. Santilli, 28326 Gates Mill Blvd., Pepper Pike, OH (US) 44124

( * ) Notice: Subject to any disclaimer, the term of this patent is extended or adjusted under 35 U.S.C. 154(b) by 61 days.

This patent is subject to a terminal disclaimer.

(21) Appl. No.: 11/870,916

(22) Filed: Oct. 11, 2007

(65) Prior Publication Data

US 2008/0029102 A1 Feb. 7, 2008

Related U.S. Application Data

(63) Continuation of application No. 10/808,211, filed on Mar. 24, 2004, now Pat. No. 7,305,991, and a continuation-in-part of application No. PCT/US03/18255, filed on Jun. 10, 2003.

(60) Provisional application No. 60/386,758, filed on Jun. 10, 2002, provisional application No. 60/456,552, filed on Mar. 24, 2003, provisional application No. 60/457,513, filed on Mar. 25, 2003.

(51) Int. Cl.
*A61B 19/00* (2006.01)
(52) U.S. Cl. ...................... 128/849; 128/852
(58) Field of Classification Search .......... 128/849–856
See application file for complete search history.

(56) References Cited

U.S. PATENT DOCUMENTS

| | | |
|---|---|---|
| 3,030,957 A | 4/1962 | Melges |
| 3,410,266 A | 11/1968 | Krzewinski et al. |
| 3,452,750 A | 7/1969 | Blanford |
| 3,494,356 A | 2/1970 | Melges |
| 3,589,365 A | 6/1971 | Sejman |
| 3,693,618 A | 9/1972 | Madden |

(Continued)

*Primary Examiner*—Michael A. Brown
(74) *Attorney, Agent, or Firm*—Wayne D. Porter, Jr.

(57) ABSTRACT

A surgical drape includes a first, closed container within which a first sheet is disposed. The first sheet has first and second opposed ends, the first end of the first sheet being removable from the container so as to remove a desired portion of the first sheet from the container, the second end of the first sheet remaining within the container. Preferably, the first container is laid across a desired portion of the table prior to placing the patient on the table. After the patient has been positioned properly and prepped, the first sheet can be pulled from underneath the patient and pulled out of the first container so that the sheet covers the table in the area of surgical interest and then covers the entire side or end of the table down to the floor. After the surgical procedure has been completed, the first sheet and the container can be removed and discarded. Desirably, the surface of the container in contact with the table is provided with adhesive that will prevent undesired movement of the container relative to either the table or the patient. If desired, the edges of the first sheet can be provided with adhesive surfaces, or possibly hook and loop fasteners, in order to secure the edges of the first sheet to selected portions of the operating table. Alternative embodiments include a second sheet that can be used to cover other portions of the operating table and a third sheet that can be used to cover portions of the patient during pre-operation preparations.

14 Claims, 6 Drawing Sheets

U.S. PATENT DOCUMENTS

| | | | |
|---|---|---|---|
| 3,902,484 A * | 9/1975 | Winters | 128/849 |
| 3,911,912 A | 10/1975 | Krebs et al. | |
| 3,930,497 A | 1/1976 | Krebs et al. | |
| 3,942,523 A | 3/1976 | Rudtke | |
| 3,954,174 A * | 5/1976 | Kraus | 206/572 |
| 3,998,221 A | 12/1976 | Collins | |
| 4,119,093 A | 10/1978 | Goodman | |
| 4,334,529 A | 6/1982 | Wirth | |
| 4,349,019 A | 9/1982 | Singer | |
| 4,352,429 A * | 10/1982 | Newman | 206/439 |
| 4,354,486 A | 10/1982 | Oliver | |
| 4,414,968 A | 11/1983 | Amin | |
| 4,471,769 A | 9/1984 | Lockhart | |
| 4,479,492 A | 10/1984 | Singer | |
| 4,520,807 A | 6/1985 | Rotter | |
| 4,570,628 A | 2/1986 | Neal | |
| 4,627,426 A | 12/1986 | Wegener et al. | |
| 4,905,710 A | 3/1990 | Jones | |
| 4,927,073 A * | 5/1990 | Esposito | 229/117.07 |
| 5,069,907 A * | 12/1991 | Mixon et al. | 424/445 |
| 5,392,917 A * | 2/1995 | Alpern et al. | 206/570 |
| 5,618,278 A | 4/1997 | Rothrum | |
| 5,649,550 A * | 7/1997 | Crook | 128/849 |
| 6,244,268 B1 | 6/2001 | Annett et al. | |
| 2002/0147091 A1 | 10/2002 | Healy et al. | |

* cited by examiner

SURGICAL DRAPE

REFERENCE TO RELATED APPLICATIONS

The present application is a continuation-in-part of International Application PCT/US03/18255, filed Jun. 10, 2003. The present application claims priority from, and incorporates by reference, the following United States Provisional Patent Applications: Ser. No. 60/386,758 filed Jun. 10, 2002; Ser. No. 60/456,552 filed Mar. 24, 2003; and Ser. No. 60/457,513, filed Mar. 25, 2003.

BACKGROUND OF THE INVENTION

1. Field of the Invention.

The invention relates to surgical drapes and, more particularly, to a surgical drape for protecting a patient and portions of an operating table.

2. Description of the Prior Art.

Currently, after a patient is placed on an operating table in preparation for surgery, the patient must be lifted or otherwise maneuvered in order to position drapes under the patient. This can result in random sterilization or inadequate isolation of certain portions of the patient from the surgical table. Moreover, considerable difficulty in properly positioning the drapes can be experienced. Any time spent in properly positioning the drapes can undesirably increase the amount of time required to perform the surgical procedure.

Desirably, a surgical drape would be available that would minimize or eliminate difficulties in placing drapes under a patient while isolating the surgical field in a sterile manner. Any such drape hopefully would be easy to use and would permit the surgical procedure to be performed with minimal delay.

SUMMARY OF THE INVENTION

In response to the foregoing concerns, the present invention provides a new and improved surgical drape. In a first embodiment, the surgical drape according to the invention comprises a first, closed container having a portion that can be selectively opened to form a first opening, the first container being of a size and shape such that a patient can be placed atop the first container when the first container is placed on the upper surface of the operating table. The invention includes a first sheet disposed within the first container, the first sheet having first and second opposed ends, the first end of the first sheet being removable from the first container through the first opening so as to remove a desired portion of the first sheet from the container, the second end of the first sheet remaining within the container.

Preferably, the first sheet is folded in a plicated (accordion-like) manner for compact disposition within the first container and the first container is laid across a desired portion of the table prior to placing the patient on the table. After the patient has been positioned properly and prepped, the first sheet can be pulled from underneath the patient and pulled out of the first container so that the sheet covers the table in the area of surgical interest and then covers the side or end of the table down to the floor. After the surgical procedure has been completed, the first sheet and the container from which it was pulled can be removed and discarded readily.

In the preferred embodiment, one surface of the container is provided with one or more adhesive surfaces that will secure the container to the upper surface of the operating table, thereby preventing undesired movement of the container relative to either the table or the patient. Desirably, the adhesive will be exposed by the removal of a non-stick protective layer. Also, the leading edge of the sheet desirably is provided with a pull tab. The sheet can be made of a wide variety of sterilizable materials, typically fluid-impervious, such as polyethylene or vinyl. If desired, the edges of the sheet can be provided with adhesive surfaces, or possibly hook and loop fasteners, in order to secure the edges of the sheet to selected portions of the operating table.

In a second embodiment, the first embodiment is modified to include a second sheet having first and second opposed ends. Preferably, the second end of the second sheet is connected to the second end of the first sheet disposed within the first container. The first end of the second sheet is movable relative to the second end of the second sheet so as to expose a desired portion of the second sheet. In this embodiment of the invention, a second, closed container is provided. The first sheet, the first container, and the second sheet are disposed within the second container. The second container has a portion that can be selectively opened to permit the contents of the second container to be removed therefrom. It is expected that the second sheet will be provided with adhesive surfaces in order to removably attach the second sheet to the operating table. Preferably, the second sheet is relatively thick and soft, such that it can be disposed over a substantial portion of the operating table in order to provide comfort to the patient as well as to provide protection for the table. Desirably, the second sheet is made of a first ply made of netting material, a second ply made of an adsorbent pulp material, and a third ply made of a fluid-impervious material such as polyethylene or vinyl.

In a third embodiment, a third sheet is provided. The third sheet can be used with either the first or the second embodiment or even a conventional surgical drape. The third sheet preferably is fluid-impervious and has first and second ends. The second end of the third sheet is connected to a selected one of the first container, the second end of the first sheet, or the second end of the second sheet in the region of the connection between the first container and the second sheet. The first end of the third sheet includes a cut-out portion that permits the third sheet to be fitted about a selected portion of the patient. Preferably, the third sheet is provided with a layer of adhesive about its periphery in order to permit the third sheet to be removably attached to the patient. Desirably, the connection between the third sheet and a selected one of the first container, the first sheet, or the second sheet is severable such that the third sheet can be removed and discarded when desired, such as after initial pre-operative preparation work on the patient has been completed.

The surgical drape according to the invention is usable with various attachments and devices that commonly are used in conjunction with such drapes. For example, the invention can be used with a conventional pouch-like container made of a lightweight, flexible material, the pouch-like container having a large opening at a first end and a small, selectively openable valve at a second end. The pouch-like container has a layer of adhesive adjacent the large opening that permits the pouch-like container to be attached to, and removed from, a selected portion of the first sheet or the first container.

By using the surgical drape according to the invention, the drape can be positioned on the upper surface of the operating table in a desired position prior to placing the patient thereon. Accordingly, merely by opening the first container, the first sheet can be withdrawn from the container and both it and the second sheet, if provided, can be extended as necessary to protect the table. There no longer is a need to lift the patient once the patient has been placed on the table.

The foregoing and other features and advantages of the invention will be apparent from a review of the following description of the invention, together with the attached drawings.

DESCRIPTION OF THE PREFERRED EMBODIMENT

Figure 1:
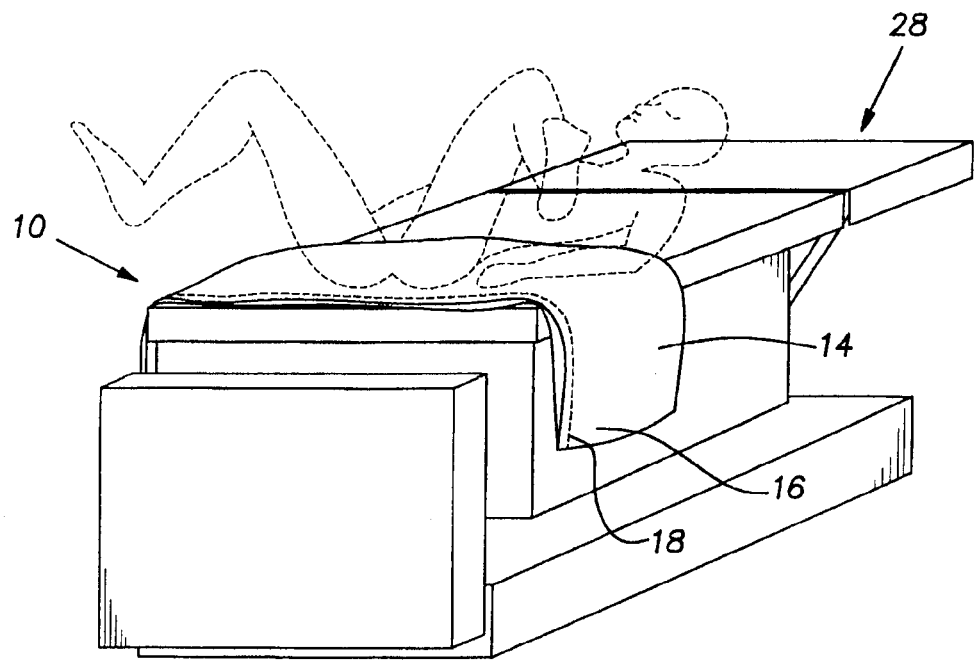
FIG. 1 is a view of a first embodiment of a surgical drape according to the invention disposed at the foot of an operating table.
Figure 2:
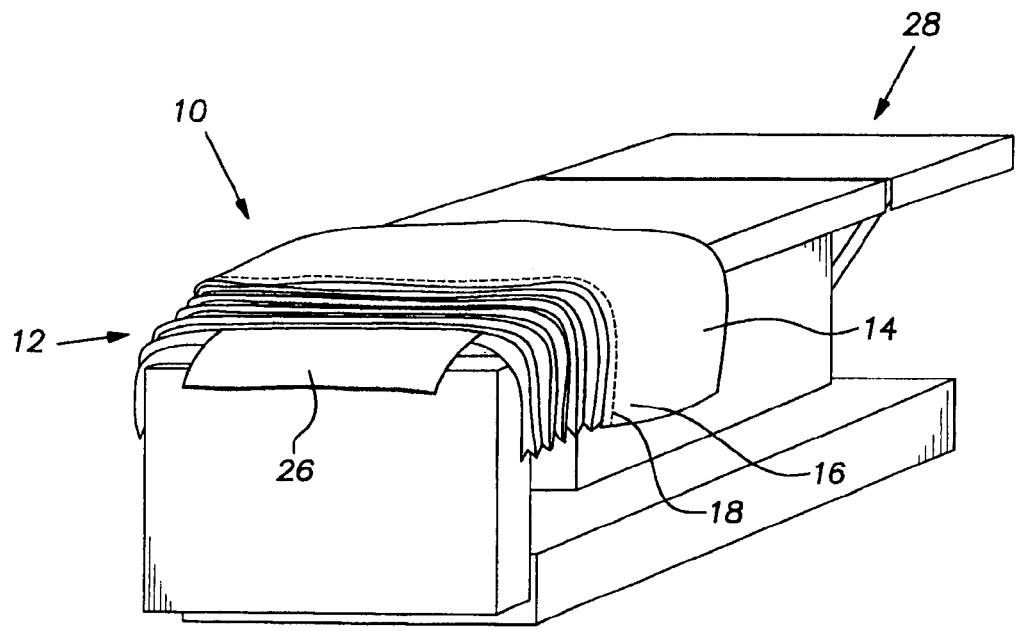
FIG. 2 is a view of the surgical drape of FIG. 1, with a first sheet partially withdrawn from an opened container.
Figure 3:
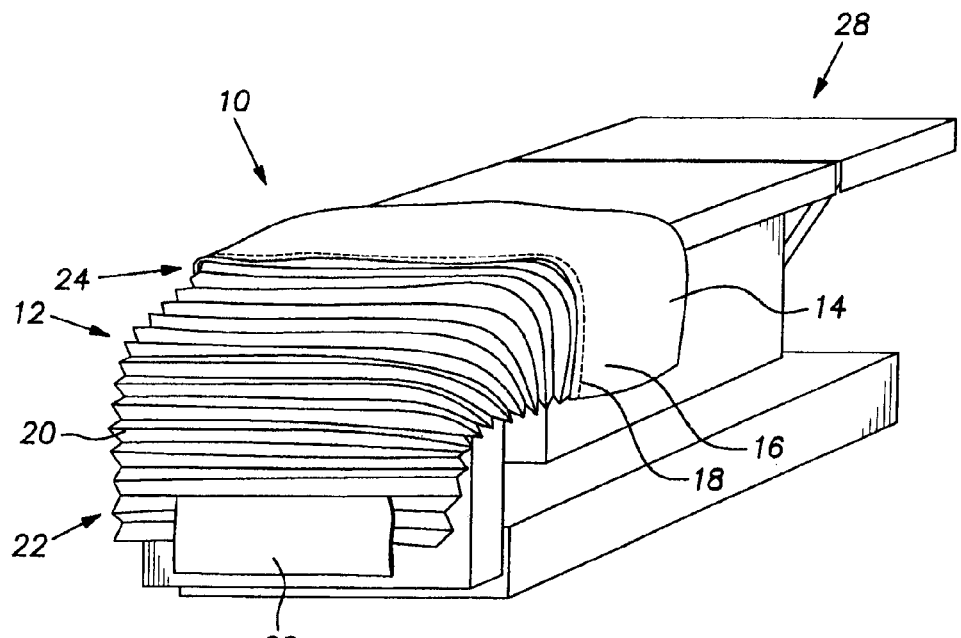
FIG. 3 is a view similar to FIG. 2 in which the first sheet has been pulled further from the container.
Figure 4:
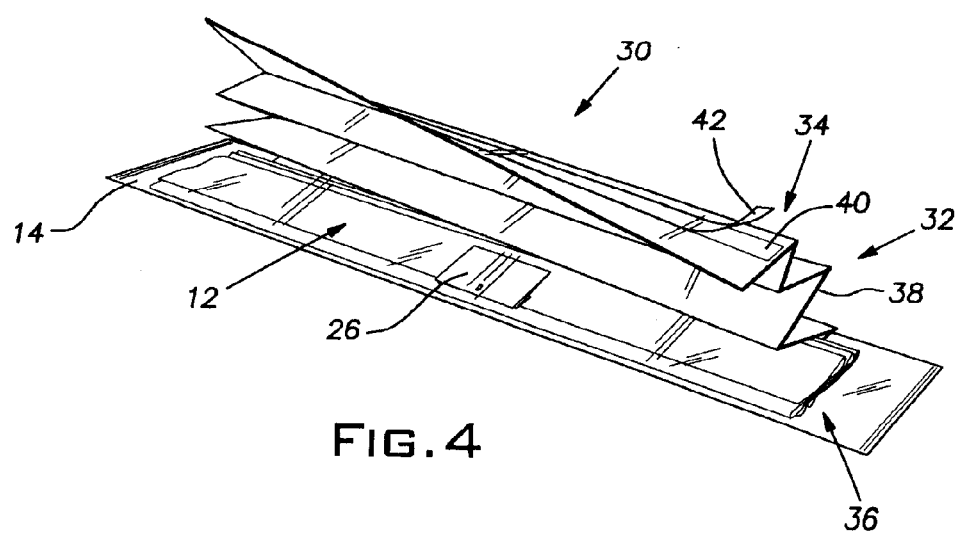
FIG. 4 is a perspective view of a second embodiment of the invention with a second sheet in the process of being expanded.

Referring generally to FIGS. 1-3, a first embodiment of a surgical drape according to the invention is indicated generally by the reference numeral 10. The drape 10 is illustrated as being used for perineal surgery, where the portion of the patient being operated on is positioned at the foot of an operating table 28. The drape 10 could be used for surgical procedures on any part of a patient's body, such as the head (head of the operating table 28) and upper extremities (sides of the operating table 28), and so forth.

The drape 10 includes a first sheet 12 that is disposed in a first, elongate, flexible container 14. The container 14 has an end portion 16 that is connected to the remainder of the container 14 by a series of scores 18. The sheet 12 is folded in plicated (accordion-like) fashion to form a series of pleats 20. The pleats 20 are arranged so that the sheet 12 can be withdrawn from the container 14 after the end portion 16 has been opened.

Figure 6:
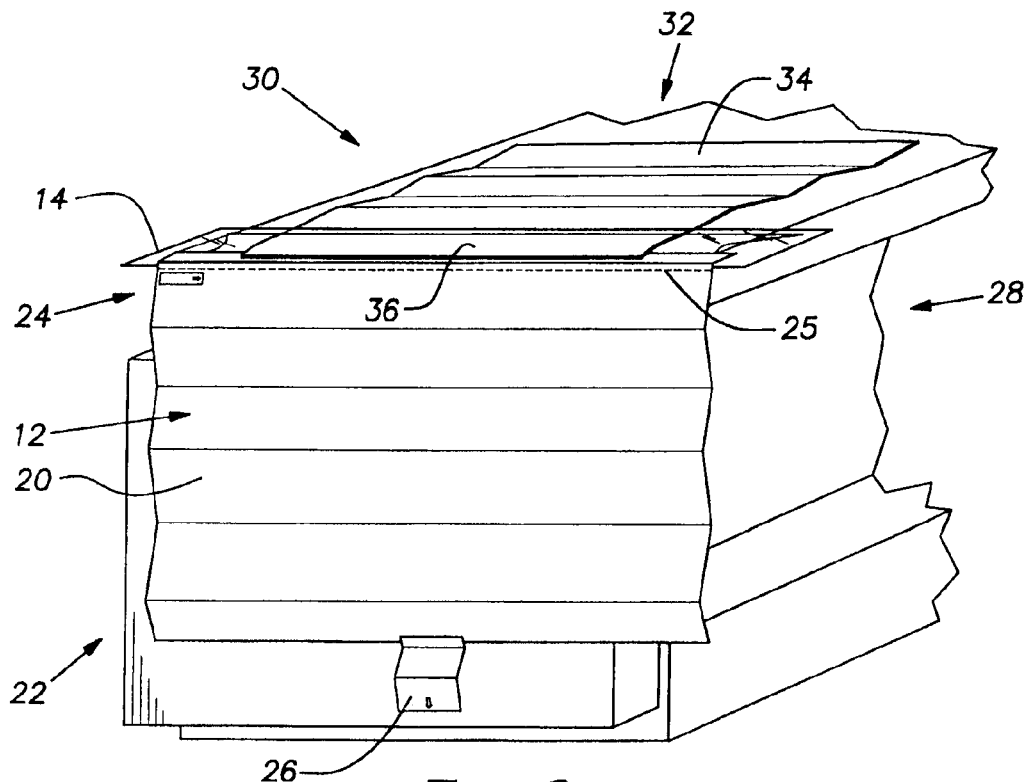
FIG. 6 is a view similar to FIG. 5 in which the first sheet has been fully pulled from the container.

The sheet 12 has a first end 22 and a second, opposed end 24. The second end 24 is secured to the inside of the container 14. A series of perforations 25 extend across the sheet 12 near the second end 24 (see FIGS. 6-8). The first end 22 is not connected to the container 14. A small pull tab 26 of paper or other suitable material can attached to the first end 22 in order to permit a user to readily pull the sheet 12 from the container 14. The tab 26 can be colored differently than the sheet 12 in order for the user to more readily locate and grasp the tab 26. It is expected that the second end 24 will be secured within the container 14, preferably by adhesive or heat-sealing. One side of the container 14 is provided with an adhesive surface (not shown) that is protected by a removable, non-stick protective layer (not shown).

The sheet 12 can be of various sizes and shapes, or combinations of sizes and shapes, although a generally rectangular shape is preferred for ease of manufacture. For example, the sheet 12 can be in the form of a trapezoid in which the smaller end of the sheet 12 remains disposed within the container 14 or a combination of a smaller upper rectangular portion connected to a larger lower rectangular or trapezoidal portion. The actual dimensions of the sheet 12 will be selected to fit the dimensions of the operating table 28 and the type of surgical procedure being performed.

The sheet 12 preferably is made of commercially available polyethylene sheeting, about 0.003 inch thick, which can be sterilized. There are other materials that are suitable for the sheet 12, such as various types of vinyl. Regardless of the material from which it is made, the sheet 12 preferably is fluid-impervious. The container 14 preferably is made of a sterilizable, transparent, fluid-impervious material such as polyethylene or vinyl. It is expected that the sheet 12 will be in a sterile condition while it remains in the unopened container 14. If desired, the sheet 12 can be provided with adhesive portions, or possibly hook and loop fasteners, at selected places in order to attach the sheet 12 to the operating table after the sheet 12 has been pulled from the container 14. The pull tab 26 also can be provided with adhesive portions, if desired.

In use, the non-stick layer covering the adhesive surface on the container 14 is removed and the container 14 is placed atop the operating table 28 in a desired location. For example, if the drape 10 is to be used for perineal surgery, the container 14 will be placed at or near the foot of the table 28. The container 14 extends toward the floor approximately 24 inches on either side of the table 28. The container 14 is positioned such that the first end 22 is closest to the end of the table 28. The adhesive surfaces on the container 14 will prevent the container 14 from moving relative to the table 28.

The patient is placed atop the table 28 with the patient's buttocks or lumbar spine region on the upper surface of the container 14. An opening is formed in the container 14 by pulling on the portion 16. The container 14 is severed in the region of the scores 18. If the pull tab 26 is attached to the first end 22, pulling the tab 26 toward the floor will pull the sheet 12 along with it. Alternatively, if the pull tab 26 has not been used, the first end 22 is grasped and pulled, whereupon the sheet 12 can be withdrawn from the container 14 and positioned appropriately to cover the end and sides of the table 28. If adhesive portions have been included as part of the edges of the sheet 12 and/or the tab 26, the sheet 12 can be attached to the table 28 in order to prevent undesired movement of the sheet 12 during the surgical procedure. After the surgical procedure has been completed, the sheet 12 can be severed along the perforations 25 and discarded. The remainder of the drape 10 can be removed and discarded after the patient has been removed from the table 28.

A Second Embodiment

Referring generally to FIGS. 4-6 and 10-11, a surgical drape according to a second embodiment of the invention is indicated by the reference numeral 30. The drape 30 is substantially identical to the drape 10, with the following exceptions. The drape 30 includes a second sheet 32 that has first and second opposed ends 34, 36. The second end 36 is connected to the second end 24 of the sheet 12 disposed within the container 14, preferably by adhesive or heat-sealing. The remainder of the sheet 32 remains outside the container 14. In a manner similar to the first sheet 12, the second sheet 32 is folded to form pleats 38. The first end 34 is movable relative to the second end 36 so as to expose a desired number of pleats 38. The second sheet 32 preferably has one or more adhesive surfaces 40 that are protected by removable layers 42 on that side that faces the upper surface of the operating table 28.

A second, closed container 44 is provided. The first sheet 12, the first container 14, and the second sheet 32 are disposed within the container 44. The container 44 has a sealed closure 46 that can be selectively opened to permit the contents thereof to be removed from the container 44. It is expected that the contents of the container 44 will be sterilized and will remain in that condition until the closure 46 is opened.

The second sheet 32 preferably is made of a sterilizable, relatively soft material. It is possible to make the second sheet 32 from a first ply of netting material, a second ply made of an absorbent pulp material, and a third ply of a fluid-impervious material such as polyethylene or vinyl. If sterilization is not critical, the container 44 can be made of the same material at that from which the container 14 is made. Preferably, however, the container 44 is be made of two materials—a backing sheet that is porous to a sterilizing gas such as ethylene oxide and a facing sheet of a transparent, non-porous material such as mylar or clear polyethylene. The container 44 is commercially available and is referred to as a "sterilization pouch."

Figure 5:
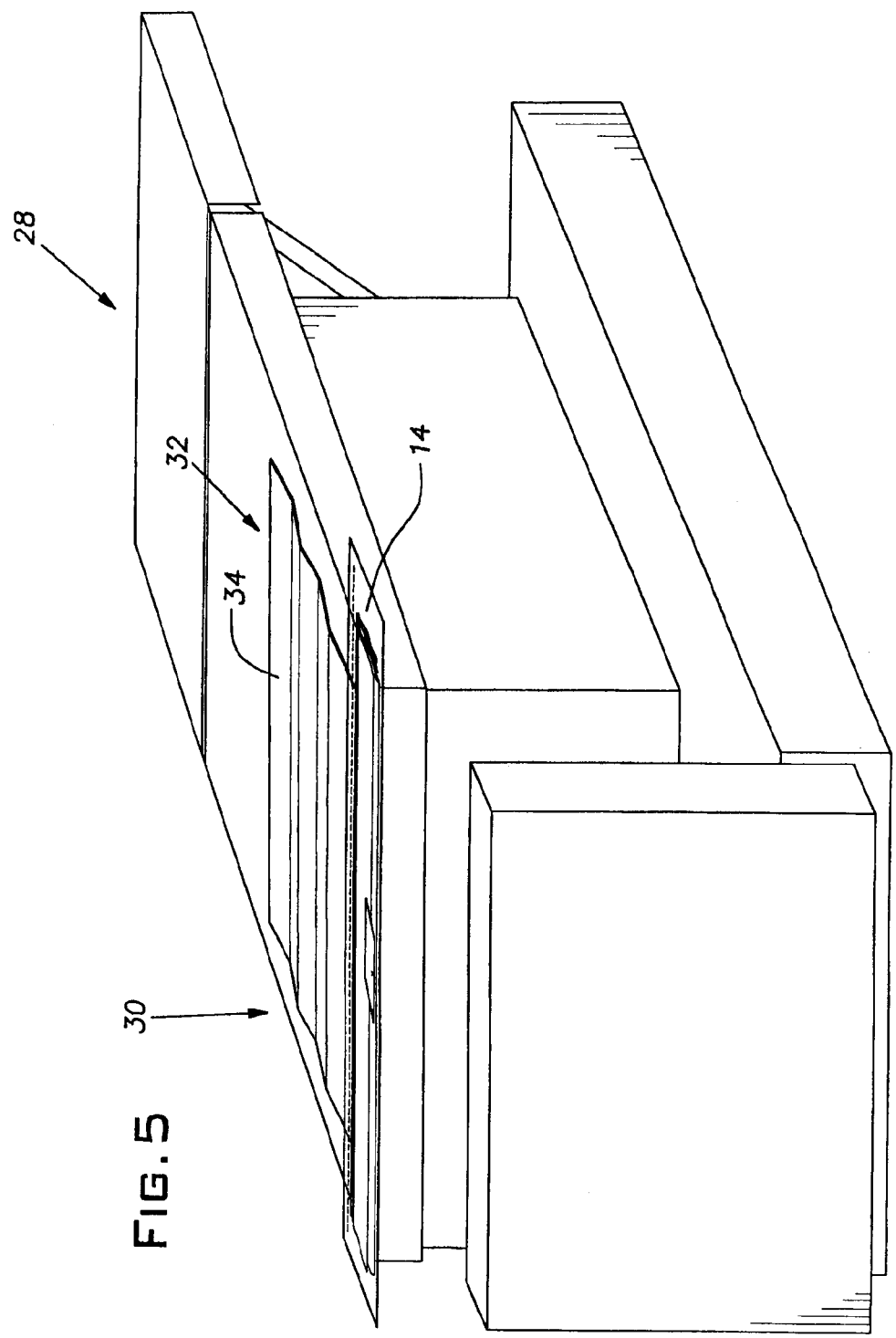
FIG. 5 is a view of the surgical drape of FIG. 4 atop an operating table.

In use, the sheet 32 is moved to that position shown in FIG. 5 and is secured in place on the upper surface of the operating table 28 by the exposed adhesive surfaces 40. Thereafter, the sheet 12 and the container 14 are positioned as described previously and as shown in FIG. 6. After the surgical procedure has been completed, the sheet 12 can be removed from the remainder of the drape 30 and discarded. Then, after the patient has been removed from the table 28, the container 14 and the second sheet 32 can be removed and discarded.

A Third Embodiment

Figure 7:
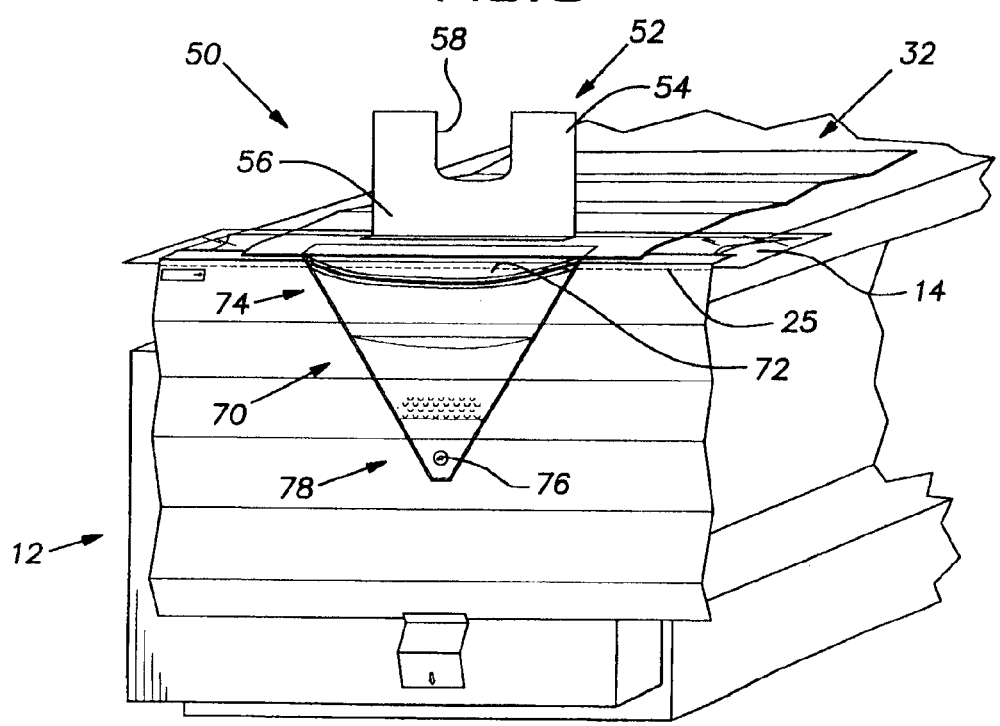
FIG. 7 is a view similar to FIG. 6 showing a third embodiment of the invention in which a third sheet is provided.
Figure 8:
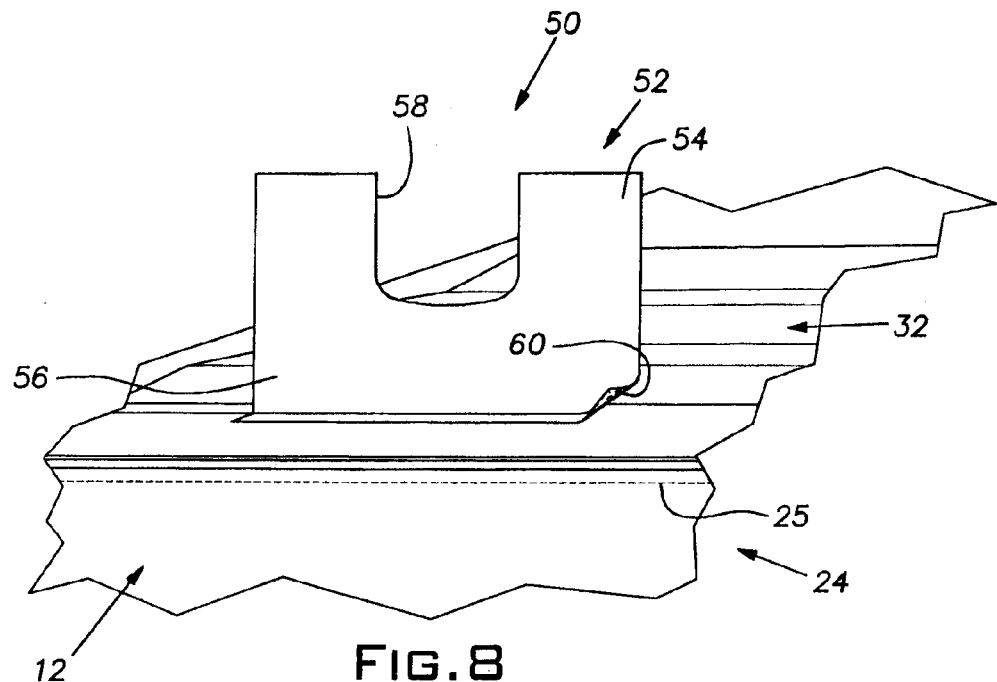
FIG. 8 is an enlarged view of a portion of the drape of FIG. 7 showing the third sheet partially severed from the remainder of the drape.
Figure 9:
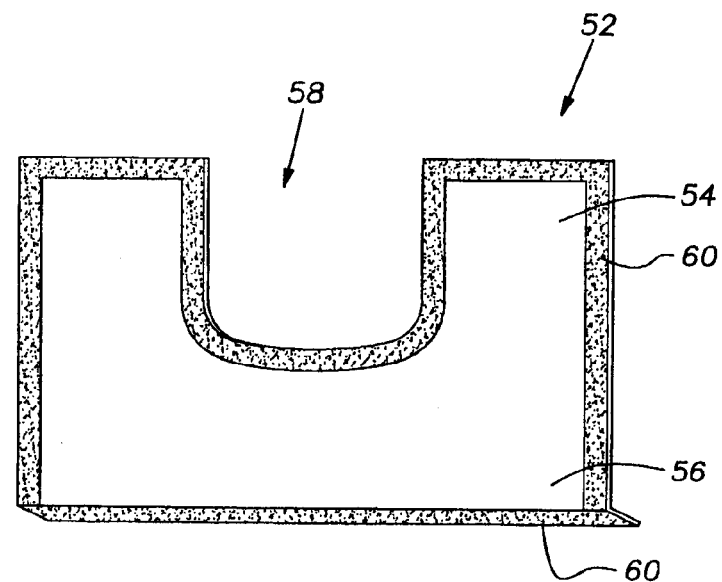
FIG. 9 is a view of the third sheet from the opposite side shown in FIG. 8 and illustrating adhesive applied to the third sheet.
Figure 10:
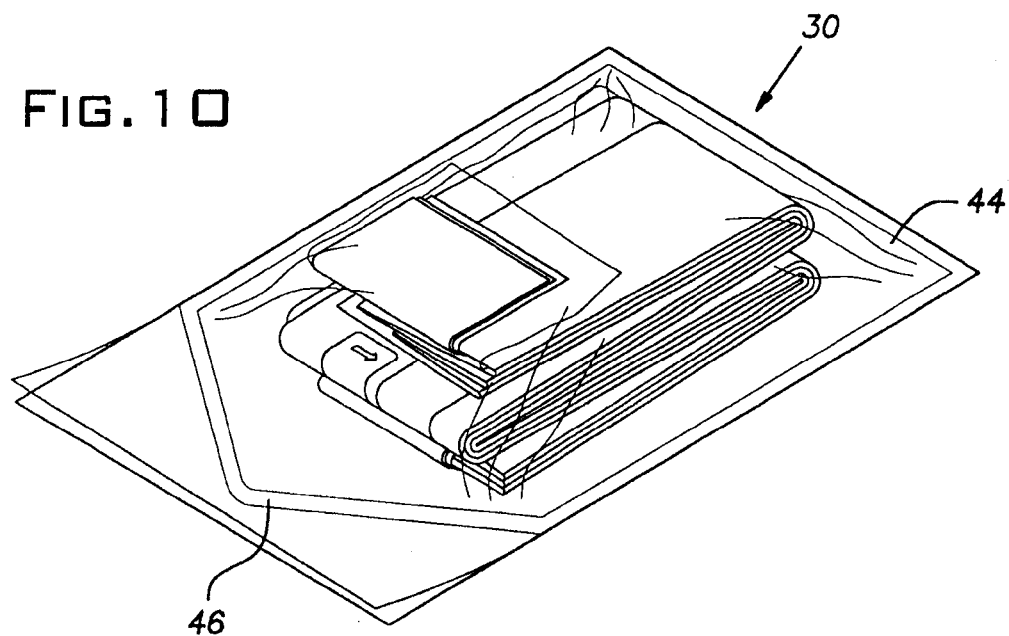
FIG. 10 is a view of the surgical drape of FIG. 4 packaged in a second container.
Figure 11:
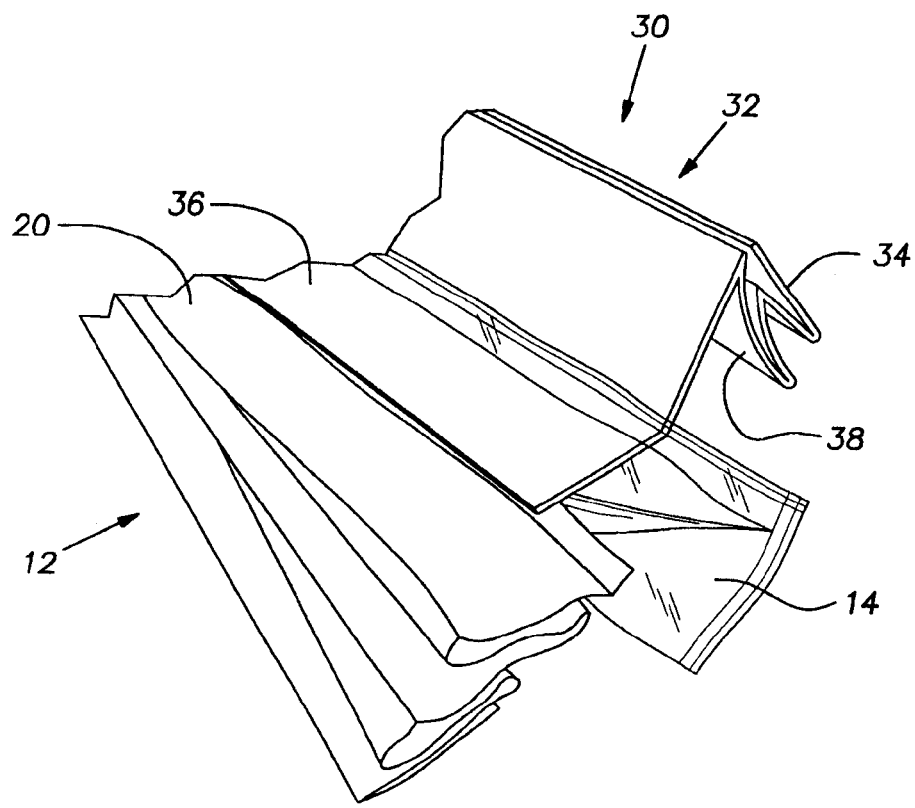
FIG. 11 is an enlarged view of a portion of FIG. 4 showing the surgical drape in the process of being opened.

Referring to FIGS. 7-9, a surgical drape according to a third embodiment of the invention is indicated by the reference numeral 50. The drape 50 is substantially identical to the drapes 10, 30, with the following exceptions. The drape 50 includes a third sheet 52 that preferably is made of a fluid-impervious material such as polyethylene or vinyl. The sheet 52 has first and second opposed ends 54, 56. The second end 56 is connected to a selected one of the first container 14, the second end 24 of the first sheet 12, or the second end 36 of the second sheet 32 in the region of the connection between the first container 14 and the second sheet 32. The first end 54 is movable relative to the second end 56 so as to cover a desired portion of the patent. Such covering is facilitated by a cut-out portion 58. The third sheet 52 preferably has adhesive surfaces 60 on its periphery that are protected by removable layers (not shown) on that side that faces the patient. The adhesive surfaces 60 that are expected to contact the patient are made of double-sided tape that employ patient contact grade adhesive.

It is expected that the sheet 52 will be attached directly to the patient during pre-operation preparations by means of the adhesive surfaces 60. After such preparations have been completed, the sheet 52 can be removed from the patient. Then, the second end 56 can be severed from the remainder of the drape 50 (see FIG. 8) and discarded. The remaining portions of the drape 50 will remain in place while the surgical procedure is performed. After the surgical procedure has been completed, the drape 50 can be removed and discarded as described previously for the drapes 10, 30.

With continued reference to FIG. 7, a pouch-like container 70 can be used with any of the drapes 10, 30, 50. The container 70 has a large opening 72 at a first end 74 and a small, selectively openable valve 76 at a second end 78. The container 70 includes a layer of adhesive adjacent the first end 74 that permits the container 70 to be attached to, and removed from, a selected portion of the first sheet 12 or the first container 14. The container 70 can be used to collect tissue, fluids and other waste materials discarded during the surgical procedure. Fluids can be withdrawn from the container 70 through a hose (not shown) connected to the valve 76. Solid materials will be retained within the container 70 for disposition after the surgical procedure has been completed. The container 70 is commercially available from Mitcrotek Medical, Inc., Columbus, Miss. 39701.

As will be apparent from the foregoing description, a surgical drape according to one of the embodiments of the invention can be positioned in any desired place on the upper surface of the operating table 28 in order to perform any desired type of surgical procedure. It is possible that two or more drapes 10 can be used at the same time to protect different portions of the operating table 28. Merely by opening the first container 14, the first sheet 12 can be withdrawn from the container 14 and extended as necessary to protect the table 28. The second sheet 32 similarly can be extended over the operating table 28. Because the drape 10 is pre-positioned on the table 28, there no longer is a need to lift the patient once the patient has been placed on the table 28.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A surgical drape for use in conjunction with an operating table having an upper surface upon which a patient can be placed, an end, and side edges, comprising:

a first, closed container having a portion that can be selectively opened to form a first opening, the first container being of a size and shape such that a patient can be placed atop the first container when the first container is placed on the upper surface;

a first sheet disposed within the first container, the first sheet having first and second opposed ends, the first end of the first sheet being removable from the first container through the first opening so as to remove a desired portion of the first sheet from the container, the second end of the first sheet remaining within the container;

a pouch-shaped container made of a lightweight, flexible material, the pouch-shaped container having a large opening at a first end and a small, selectively openable opening at a second end, the pouch-shaped container further comprising a layer of adhesive adjacent the large opening that permits the pouch-shaped container to be attached to, and removed from, a selected portion of the first sheet or the first container;

the first container, the first opening, and the first sheet being sufficiently long that they extend beyond the side edges of the operating table; and wherein, upon opening the first container while the patient is placed thereon, the first sheet can be extended to cover the end and a portion of the side edges of the operating table.

2. The surgical drape of claim 1, wherein the first sheet is made of a fluid-impervious material.

3. The surgical drape of claim 1, wherein the first container is made of a fluid-impervious material.

4. The surgical drape of claim 1, further comprising a pull tab attached to the first end of the first sheet.

5. The surgical drape of claim 1, wherein the first sheet is folded within the first container in a plicated manner.

6. The surgical drape of claim 1, wherein the selectively openable portion is defined by scores.

7. The surgical drape of claim 1, further comprising an adhesive surface on the outer surface of the first container and a removable protective layer disposed over the adhesive surface, the adhesive surface being exposed upon removal of the protective layer, the adhesive surface being attachable to the upper surface of the operating table to prevent movement of the first container relative thereto.

8. A surgical drape for use in conjunction with an operating table having an upper surface upon which a patient can be placed, an end, and side edges, comprising:
   a first, closed container having a portion defined by scores that can be selectively opened to form a first opening, the first container being of a size and shape such that a patient can be placed atop the first container when the first container is placed on the upper surface, the first container being made of a fluid-impervious material;
   a first sheet disposed within the first container, the first sheet being folded within the first container in a plicated manner and having first and second opposed ends, the first end of the first sheet being removable from the first container through the first opening so as to remove a desired portion of the first sheet from the container, the second end of the first sheet remaining within the container, the first sheet being made of a fluid-impervious material;
   a pull tab attached to the first end of the first sheet;
   an adhesive layer on the outer surface of the first container;
   a removable protective strip disposed over the adhesive layer, the adhesive layer being exposed upon removal of the protective strip, the adhesive layer being attachable to the upper surface of the operating table to prevent movement of the first container relative thereto;
   the first container, the first opening, and the first sheet being sufficiently long that they extend beyond the side edges of the operating table; and
   wherein, upon opening the first container while the patient is placed thereon, the first sheet can be extended to cover the end and a portion of the side edges of the operating table.

9. The surgical drape of claim 8, further comprising:
   a second sheet for protecting portions of a patient, the second sheet including:
      a first end that conforms generally to the shape of a selected portion of the patient; and
      a second end that is attachable to the first sheet or the first container, the attachment between the second end and the first sheet or the first container being severable so that the second sheet can be removed and discarded when desired.

10. The surgical drape of claim 9, wherein the second sheet is made of a fluid-impervious material.

11. The surgical drape of claim 9, further comprising a layer of adhesive about the periphery of the second sheet that permits the second sheet to be attached to the patient.

12. A surgical drape for use in conjunction with an operating table having an upper surface upon which a patient can be placed, an end, and side edges, comprising:
   a first, closed container having a portion that can be selectively opened to form a first opening, the first container being of a size and shape such that a patient can be placed atop the first container when the first container is placed on the upper surface;
   a first sheet disposed within the first container, the first sheet having first and second opposed ends, the first end of the first sheet being removable from the first container through the first opening so as to remove a desired portion of the first sheet from the container, the second end of the first sheet remaining within the container;
   a second sheet for protecting portions of a patient, the second sheet including:
      a first end that conforms generally to the shape of a selected portion of the patient; and
      a second end that is attachable to the first sheet or the first container, the attachment between the second end and the first sheet or the first container being severable so that the second sheet can be removed and discarded when desired;
   the first container, the first opening, and the first sheet being sufficiently long that they extend beyond the side edges of the operating table; and
   wherein, upon opening the first container while the patient is placed thereon, the first sheet can be extended to cover the end and a portion of the side edges of the operating table.

13. The surgical drape of claim 12, wherein the second sheet is made of a fluid-impervious material.

14. The surgical drape of claim 12, further comprising a layer of adhesive about the periphery of the second sheet that permits the second sheet to be attached to the patient.

* * * * *